United States Patent
El-Husayni

[19]

[11] Patent Number: 5,940,784
[45] Date of Patent: Aug. 17, 1999

[54] HEAT FLOW METER INSTRUMENTS

[75] Inventor: Hani A. El-Husayni, Fall River, Mass.

[73] Assignee: Metrisa, Inc., Bedford, Mass.

[21] Appl. No.: 08/972,801

[22] Filed: Nov. 18, 1997

Related U.S. Application Data

[63] Continuation of application No. 08/612,581, Mar. 8, 1996, abandoned.

[51] Int. Cl.$^6$ .................................................. G01N 25/18
[52] U.S. Cl. .............................. 702/130; 374/43; 62/3.7; 62/3.3; 73/204.19
[58] Field of Search ............................... 702/130, 85, 89; 62/3.7, 3.3; 374/44, 30, 204.19; 73/204.15; 161/185

[56] References Cited

U.S. PATENT DOCUMENTS

| | | | |
|---|---|---|---|
| 3,733,887 | 5/1973 | Stanley et al. | 73/15 A |
| 4,232,543 | 11/1980 | Eguchi et al. | 73/15 A |
| 4,283,935 | 8/1981 | Eguchi et al. | 73/15 A |
| 4,304,119 | 12/1981 | Uchigaki | 73/17 R |
| 4,327,573 | 5/1982 | Jennings | 374/10 |
| 4,553,852 | 11/1985 | Derderian et al. | 374/1 |
| 4,630,938 | 12/1986 | Piórkowska-Palczewska et al. | 374/44 |
| 4,719,344 | 1/1988 | Hiroyuki | 250/203 R |
| 5,005,985 | 4/1991 | Poórkowska-Galeska et al. | 374/44 |
| 5,038,304 | 8/1991 | Bonne | 364/571.01 |
| 5,258,929 | 11/1993 | Tsuchida | 364/557 |
| 5,297,868 | 3/1994 | Graebner | 374/44 |
| 5,339,687 | 8/1994 | Gimson et al. | 73/204.19 |
| 5,544,487 | 8/1996 | Attey et al. | 62/3.7 |

FOREIGN PATENT DOCUMENTS

| | | | |
|---|---|---|---|
| 225-875 | 8/1985 | Germany . | |
| 56-037235 | 9/1982 | Japan . | |
| 57-151846 | 9/1982 | Japan | G01N 25/18 |
| 63-290949 | 5/1987 | Japan . | |
| 63-290949 | 11/1988 | Japan . | |

(List continued on next page.)

OTHER PUBLICATIONS

"Standard Practice for Calibration of the Heat Flow Meter Apparatus," ASTM Designation: C 1132–89, pp. 612–615, 1989.

(List continued on next page.)

*Primary Examiner*—Kamini Shah
*Attorney, Agent, or Firm*—Fish & Richardson P.C.

[57] ABSTRACT

An apparatus, such as, a heat flow meter instrument, for measuring thermal properties of a specimen includes a first thermoelectric device and a second thermoelectric device, each device being thermally coupled to a hot plate and a cold plate, and a heat flow transducer, thermally connectable to a specimen and constructed to measure heat flowing through the specimen. The heat flow transducer and the specimen are positionable in thermal contact between the hot plate of the first thermoelectric device and the cold plate of the second thermoelectric device. The apparatus also includes an electric power supply connected to provide controlled amounts of electric power to the first and second thermoelectric devices to maintain the plates at selected temperatures, and a processor connected to receive from the heat flow transducer a signal corresponding to the measured heat. The processor is programmed to calculate a thermal property of the specimen based on the temperatures and the measured heat. The apparatus includes a closed loop heat exchange system, thermally connecting the cold plate of the first thermoelectric device and the hot plate of the second thermoelectric device, constructed and arranged to transfer heat between the plates. The closed loop heat exchange system may include a fluid pump and a first set of conduits thermally connected to the cold plate of the first thermoelectric device and a second set of conduits thermally connected to the hot plate of the second thermoelectric device. The conduits convey a heat exchange fluid in a closed loop arrangement.

36 Claims, 12 Drawing Sheets

FOREIGN PATENT DOCUMENTS

| | | |
|---|---|---|
| 1-169346 | 7/1989 | Japan . |
| 783-664 | 11/1980 | U.S.S.R. . |
| 800-845 | 1/1981 | U.S.S.R. . |
| 911-275 | 3/1982 | U.S.S.R. . |
| 1111-083 | 8/1983 | U.S.S.R. . |
| 1485-102 | 6/1989 | U.S.S.R. . |
| 1684-643-A1 | 10/1991 | U.S.S.R. . |
| 1080435 | 8/1967 | United Kingdom . |
| 1593425 | 7/1981 | United Kingdom . |

OTHER PUBLICATIONS

"Standard Test Method for Steady–State Heat Flux Measurements and Thermal Transmission Properties by Means of the Guarded–Hot–Plate Apparatus," ASTM Designation: C 177–85, pp. 20–21, 1985.

"Section 1: Introduction," pamphlet describing the Model GHP–300 guarded hot plate thermal conductance measuring system, pp. 1 and 2, Dec. 8, 1992.

"Guarded Heat Flow Meter Instruments," pamphlet, Holometrix, Inc., 25 Wiggins Avenue, Bedford, Massachusetts 01730–2323 No Date.

"Heat Flow Meter Instruments," pamphlet, Holometrix, Inc., 25 Wiggins Avenue, Bedford, Massachusetts 01730–2323. No Date.

"Holometrix Automation Software," pamphlet, Holometrix, Inc., 25 Wiggins Avenue, Bedford, Massachusetts 01730–2323. No Date.

"Instruments for Measuring Thermal Conductivity," pamphlet, Holometrix, Inc. No Date.

"U.S. Domestic Price Schedule—R–Matic Series Heat Flow Meter Instruments for Evaluation the Thermal Performance of Insulation Materials at Full Thickness," pamphlet, Holometrix, Inc., Bedford, MA, May, 1992.

"Fox300 Thermal Conductivity Instrument," pamphlet, LaserComp, 134 Water Street, Building 3, Wakefield, Massachusetts 01880. No Date.

"An Introduction to Advance Technology: Thermal Conductivity Instrument," pamphlet, LaserComp, 134 Water Street, Building 3, Wakefield, Massachusetts 01880. No Date.

"Please Come by our Display and see the *Fastest, Most Accurate, Most Flexible,* Instruments for Testing Low Conductivity Materials," pamphlet, LaserComp, 134 Water Street, Wakefield, Massachusetts 01880. No Date.

"Thermal Conductivity Measurement Instruments: FOX50," pamphlet, LaserComp, LaserComp, 134 Water Street, Building 3, Wakefield, Massachusetts 01880. No Date.

"U.S. and Canada Price Schedule: Fox 304 Heat Flow Meter Thermal Conductivity Instrument," pamphlet, LaserComp, 60 Edgemere Road, Lynnfield, Massachusetts 01940, Apr., 1994.

"U.S. and Canada Price Schedule: Fox 600 Heat Flow Meter Thermal Conductivity Instrument," pamphlet, LaserComp, 60 Edgemere Road, Lynnfield, Massachusetts 01940, Jan. 1, 1993.

PCT Search Report dated Jun. 26, 1997 in International Patent Application No. PCT/US97/03583.

"Technical Data Sheet: Thermoelectric Cooling Module, Part Nos. 6300/127/060*," pamphlet, p. 16. No Date.

"Standard Test Method for Steady–State Heat Flux Measurements and Thermal Transmission Properties by Means of Heat Flow Meter Apparatus," ASTM Designation: C 518–91, pp. 153–164, 1991.

"Standard Practice for Calculating Thermal Transmission Properties From Steady–State Heat Flux Measurements," ASTM Designation: C 1045–90, pp. 538–544, 1990.

"Standard Practice for Evaluating Thermal Conductivity of Gasket Materials," ASTM Designation: F 433–77, pp. 431–737, 1987.

"Heat Flow Meter Thermal Conductivity Instrument—Holometrix k–Matic Models FT50 & F175," Holometrix, Inc. *Operation & Maintenance Manual,* Dec. 1, 1994.

"Heat Flow Meter Thermal Conductivity Instrument—Holometrix Rapid–k Models VT250–A, VT400–A, RK30–A & RK70–A," Holometrix, Inc. *Operation & Maintenance Manual.* No Date.

"Unitherm™ Thermophysical Testing Instruments," pamphlet of specifications of QuickLine™–16 Thermal Conductivity Measuring Instrument, pamphlet, Anter Corporation. No Date.

"Thermal Conductivity Tester Model HC–072 for Thermal Insulating and Synthetic Materials—According to ASTM C518, JIS A1412," pamphlet for EKO model HC–072, EKO Instruments Trading Co., Ltd. No Date.

HEAT FLOW METER INSTRUMENTS

This is a continuation of application Ser. No. 08/612,581, filed Mar. 8, 1996, now abandoned.

BACKGROUND OF THE INVENTION

The present invention relates to heat flow meter instruments for testing thermal properties of materials including thermal conductivity and heat capacity. More particularly, the invention relates to a closed loop heat flow meter instrument that utilizes thermoelectric devices for controlling temperature.

Thermal properties, such as thermal conductivity and heat capacity, are important physical properties of solids. Heat flows through a solid that has a temperature gradient across its volume. The thermal conductivity of a specimen can be measured directly by measuring the heat flux resulting from a known temperature gradient across a known thickness. A one-dimensional form of the Fourier heat flow relation is frequently used to calculate thermal conductivity under steady-state conditions:

$$k = Q \frac{\Delta X}{\Delta T} \quad (1)$$

wherein k is thermal conductivity, Q is a heat flow per a unit surface area (heat flux), $\Delta T$ is a temperature difference over the thickness $\Delta X$. A standard instrument measures the thermal conductivity of a specimen located between two flat plates by maintaining the plates at known, but different temperatures. As heat flows through the specimen from the hot side to the cold side, a heat flux transducer measures the amount of heat transferred. A thermocouple measures the temperature of each plate.

In some instruments, the two plates are heated (or cooled) separately. Usually, each plate is heated by an electric heater, such as an etched foil heater or a wire heater, powered by an electric power supply. The plate may also be thermally connected to a heat sink with a circulating coolant. The desired plate temperature is reached by balancing the action of the heater and the cooling system. The balancing commonly causes pulsation of the temperature, and thus the plate provides pulsating amounts of heat to the specimen. To reduce the pulsating effect, a thermal buffer is frequently placed between the plate and the heat flux transducer. Therefore, it may take a relatively long time to achieve a thermal equilibrium at a desired temperature. Alternatively, each plate may be heated or cooled by regulating temperature of the fluid circulating in the heat sinks. This type of temperature regulation may increase the cost of operation. In either case, the output of the heat flux transducer and of the thermocouples is monitored until variations in temperature subside and steady-state heat conditions exist. Then, the instrument measures the thermal conductivity. The measurements are usually performed according to standard testing methods, such as, C 518 or C 1045 methods published in Annual Book of ASTM Standards.

Furthermore, a conventional electric heater may introduce a significant error to the measured data. Some instruments use a heater powered by an AC power supply. The AC signal introduces AC noise into the system. This noise affects detection of the sensor signals since they are at the microvolt levels. Therefore, to provide accurate data, the sensors may need AC shielding.

There are other methods that do not require the steady-state conditions. The thermal conductivity coefficient may be measured by so called thermal diffusivity methods and quasi-stationary methods. The thermal diffusivity methods (e.g., hot wire method, flash method) determine the thermal conductivity coefficient by indirectly measuring the time of flight of a heat pulse across a layer of the specimen. The thermal diffusivity is the ratio of the thermal conductivity, at an average temperature of the specimen, and the heat capacity. The quasi-stationary method measures usually the sum of temperature differences between the two flat surfaces of the specimen, as the heat is conducted toward the colder plate. This method assumes a linear temperature distribution inside the specimen which is an approximation of the actual behavior.

There is a need for a fast, efficient and highly accurate heat flow meter instrument, which has a relatively small size.

SUMMARY OF THE INVENTION

In general, the instrument of the present invention is a fast, efficient and highly accurate heat flow meter (HFM). The HFM instrument is constructed and arranged to control precisely temperature of a high temperature plate and a low temperature plate surrounding a specimen. Each plate includes one or more thermoelectric devices, consisting of pairs of an N-type semiconductor and a P-type semiconductor. The thermoelectric devices are powered by one or more power supplies. The heat sinks of the two thermoelectric devices are thermally connected by a closed loop heat exchange system with a circulating medium. Thus the heat rejected by the heat sink at a higher temperature can be transferred to the heat sink at a lower temperature. The heat exchange system includes a separate heater or a refrigerator used to regulate the temperature of the circulating medium, which, in turn, controls the mean temperature of the specimen. This arrangement creates an efficient and thermally stable system with relatively small heat losses. The present invention has a wide range of applications in systems that pump heat across a slab of material having its surfaces at selected temperatures.

In another aspect, an apparatus (e.g., a heat flow meter instrument) for measuring thermal properties of a specimen includes a first thermoelectric device and a second thermoelectric device, each device being thermally coupled to a hot plate and a cold plate, and a heat flow transducer, thermally connectable to a specimen, constructed and arranged to measure heat flowing through the specimen. The heat flow transducer and the specimen are positionable in thermal contact between the hot plate of the first thermoelectric device and the cold plate of the second thermoelectric device. The apparatus also includes an electric power supply connected to provide controlled amounts of electric power to the first and second thermoelectric devices to maintain the plates at selected temperatures, and a processor connected to receive from the heat flow transducer a signal corresponding to the measured heat. The processor is programmed to calculate a thermal property of the specimen based on the temperatures and the measured heat.

In another aspect, an apparatus for measuring thermal properties of a specimen includes a first thermoelectric device and a second thermoelectric device, each device being thermally coupled to a hot plate and a cold plate, and a heat flow transducer, thermally connectable to a specimen, constructed and arranged to measure heat flowing through the specimen. The heat flow transducer and the specimen are positionable in thermal contact between the hot plate of the first thermoelectric device and the cold plate of the second thermoelectric device. The apparatus also includes electric power means (e.g., one or more electric power supplies) connected to provide controlled amounts of electric power to the first thermoelectric device and the second thermoelectric device to maintain the plates at selected temperatures, a heat exchange system, thermally connecting the cold plate of the first thermoelectric device and the hot plate of the second thermoelectric device, constructed and arranged to transfer heat between the plates, and a processor connected to receive from the heat flow transducer a signal corresponding to the measured heat. The processor is further programmed to calculate a thermal property of the specimen based on the temperatures and the measured heat.

In another aspect, an apparatus for measuring thermal properties of a specimen includes a first heat generating device thermally coupled to a hot plate and a second heat generating device thermally coupled to a cold plate, a first temperature sensor and a second temperature sensor located in thermal contact with the hot plate and the cold plate, respectively, and a heat flow transducer, thermally connectable to a specimen, constructed and arranged to measure heat flowing through the specimen. The heat flow transducer and the specimen are positionable in thermal contact between the hot plate and the cold plate. The apparatus further includes at least one electric power supply connected to provide controlled amounts of electric power to the first device and the second device to maintain the plates at selected temperatures, and a processor connected to receive from the heat flow transducer a signal corresponding to the measured heat. The processor is further programmed to calculate a predicted steady-state value of a thermal property of the specimen under transient thermal conditions based on the measured heat and the temperatures.

Embodiments of the apparatus may include one or more of the following features. The thermoelectric device includes pairs of N-type and P-type semiconductors.

The apparatus may include a first temperature sensor and a second temperature sensor located in thermal contact with the hot plate of the first thermoelectric device and a cold plate of the second thermoelectric device, respectively.

The apparatus may include a heat exchange system (a closed loop system or an open loop system), thermally connected to the cold plate of the first thermoelectric device and the hot plate of the second thermoelectric device.

The apparatus may include at least one heat exchange system for providing heat to or removing heat from the cold plate thermally coupled to the specimen or the hot plate thermally coupled to the specimen.

A closed loop heat exchange system may include a first set of conduits thermally connected to the cold plate of the first thermoelectric device and a second set of conduits thermally connected to the hot plate of the second thermoelectric device, the conduits being constructed to convey a heat exchange fluid in a closed loop arrangement, and a fluid pump constructed to circulate the fluid.

The closed loop heat exchange system may further include a heater constructed to heat the heat exchange fluid to a selected temperature.

The closed loop heat exchange system may further include a refrigerator constructed to cool the heat exchange fluid to a selected temperature.

The apparatus may further include a second heat flow transducer constructed to measure a flow of heat, the first and the second heat flow transducer being arranged in thermal contact with both sides of the specimen.

The apparatus may further include a thermal guard member constructed and arranged to prevent a lateral heat loss from the sample. The thermal guard member may include a set of conduits connected to the closed loop heat exchange system and constructed to convey the heat exchange fluid.

The electric power supply of the apparatus is a current supply constructed to deliver DC current to the first thermoelectric device and the second thermoelectric device connected in series. Alternatively, the electric power supply is a voltage source connected to deliver DC voltage to the first thermoelectric device and the second thermoelectric device.

The apparatus may further include a potentiometer constructed and arranged to provide a signal corresponding to the thickness of the specimen.

The processor of the apparatus may be further arranged to calculate the thermal property under steady-state thermal conditions.

The processor may be further arranged to calculate a predicted steady-state value of the thermal property under transient thermal conditions. The processor may employ a selected equation predicting thermal behavior of the specimen under the transient thermal conditions.

The apparatus operates in the temperature range of about 263 K to 393 K, and can characterize different materials, such as, fiberglass, cellular foams, rubber polymers, composite materials, ceramics, or glasses. The tested materials have thermal resistances (R values) in the range of about 0.5 to 40 $m^2 \cdot K/W$. The apparatus has a reproducibility better than ±0.2% between different tests.

DESCRIPTION OF THE PREFERRED EMBODIMENTS

Figure 1:
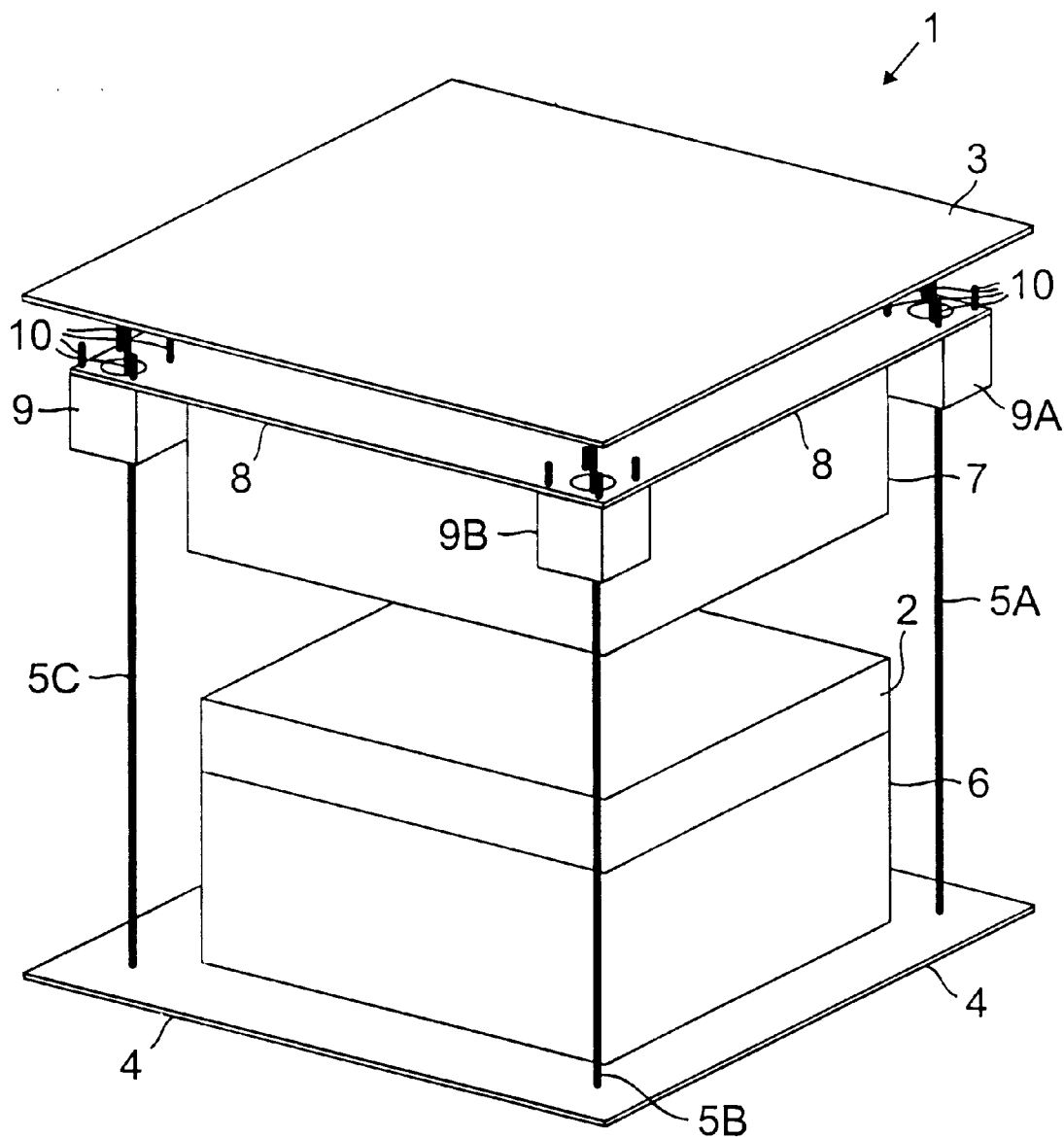
FIGS. 1 and 1A depict a schematic representation of a heat flow meter instrument for measuring thermal properties of a specimen.

FIG. 1 depicts a heat flow meter (HFM) instrument 1 for measuring thermal conductivity of a material specimen 2. HFM instrument 1 is mounted on a frame that includes an upper frame plate 3, a lower frame plate 4, and four stationary threaded rods 5A, 5B, 5C and 5D (5D is not shown). Specimen 2 is sandwitched between a lower plate assembly 6 and an upper plate assembly 7 connected to an upper support plate 8. Four stepper motors 9A, 9B, 9C and 9D (9D is not shown), connected to upper support plate 8 by sliding pins 10, ride up and down on the four stationary threaded rods. As the upper plate assembly is lowered and comes into contact with specimen 2, the sliding pins enable the four motors to continue in the downward motion so that upper plate assembly 7 contacts by gravity specimen 2. (The motors are, for example, linear actuators model ZB17GBKN-10-9, made by Eastern Air Devices, Dover, N.H.) Upper plate assembly 7 and a lower plate assembly 6 are thermally connected by a heat exchange system to create a closed thermal loop.

Figure 1A:
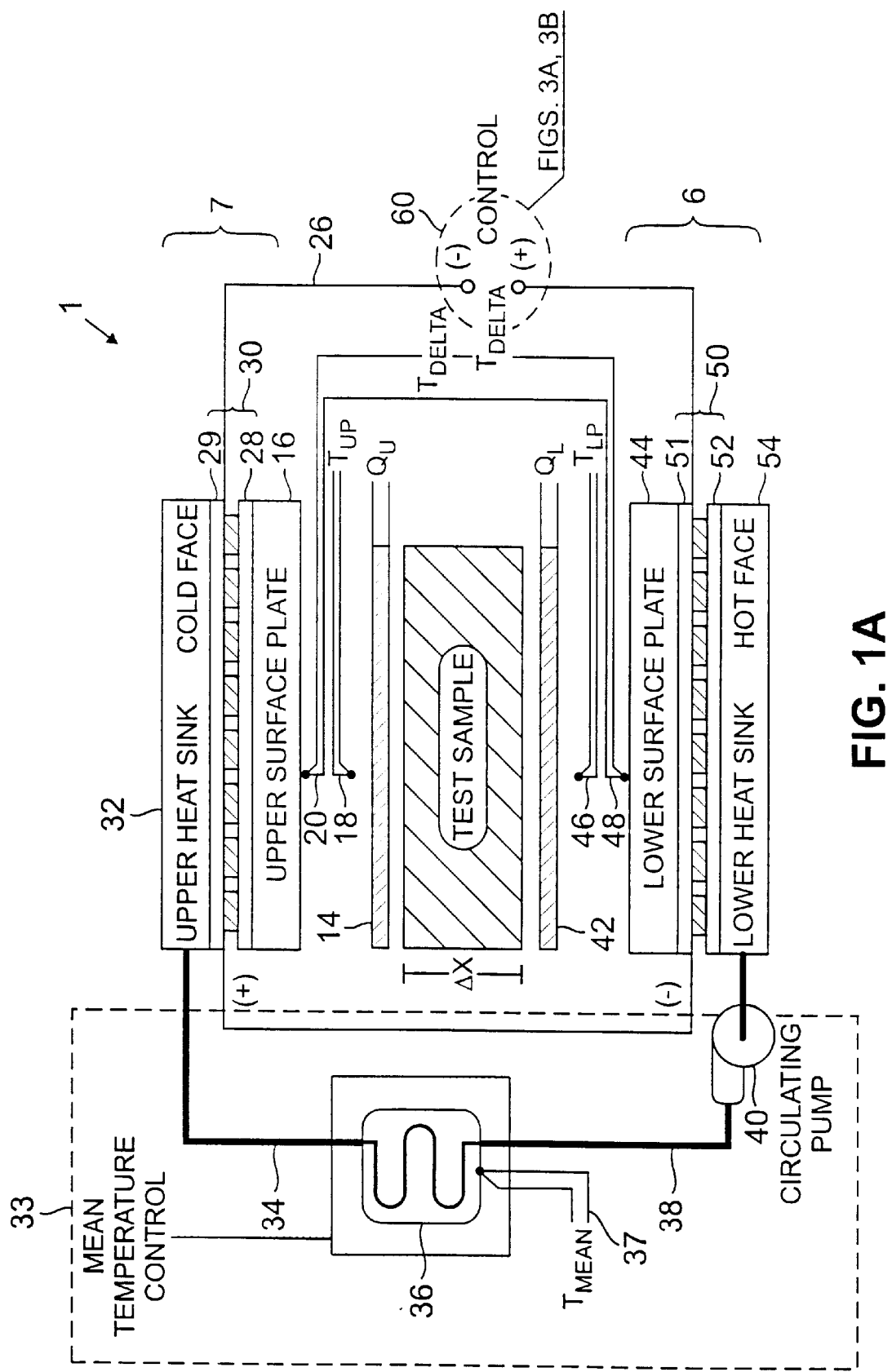

Also referring to FIG. 1A, upper plate assembly 7 is made of an upper heat flux transducer 14 thermally coupled to an upper surface plate 16, made of a material with high thermal conductivity, and thermocouples 18 and 20. Upper surface plate 16 is thermally coupled to an upper thermoelectric unit 30, which is thermally connected to an upper heat sink 32. Heat sink 32 is a flat plate with a set of conduits constructed to carry a circulating fluid. The fluid circulates in a closed fluid circuit between upper heat sink 32 and a lower heat sink 54. Similarly, the lower module includes a lower heat flux transducer 42, which is in thermal contact with specimen 2 and is thermally coupled to lower surface plate 44, made of a material with high thermal conductivity. Both heat flux transducers 14 and 42 are ITI type "A" transducers commercially available from International Thermal Instruments, Del Mar, Calif. (Other heat flux transducers can also be used, such as, transducers made by RDF Corporation of Hudson, N.H.) Thermocouples 46 and 48 measure the temperature of lower surface plate 44. Surface plate 44 is thermally coupled to a lower thermoelectric unit 50, which in turn is thermally coupled to lower heat sink 54. Lower heat sink 54, similarly as upper heat sink 32, includes a set of conduits for carrying a circulating fluid. (Instead of the thermocouples, the instrument may use a thermistor, such as, a 10 kΩ precision thermistor model YSI 44016, made by YSI Inc., Yellow Springs, Ohio, a temperature transducer AD 590 made by Analog Devices Inc., Norwood, Mass., or any other device that can measure temperature.)

Figure 2:
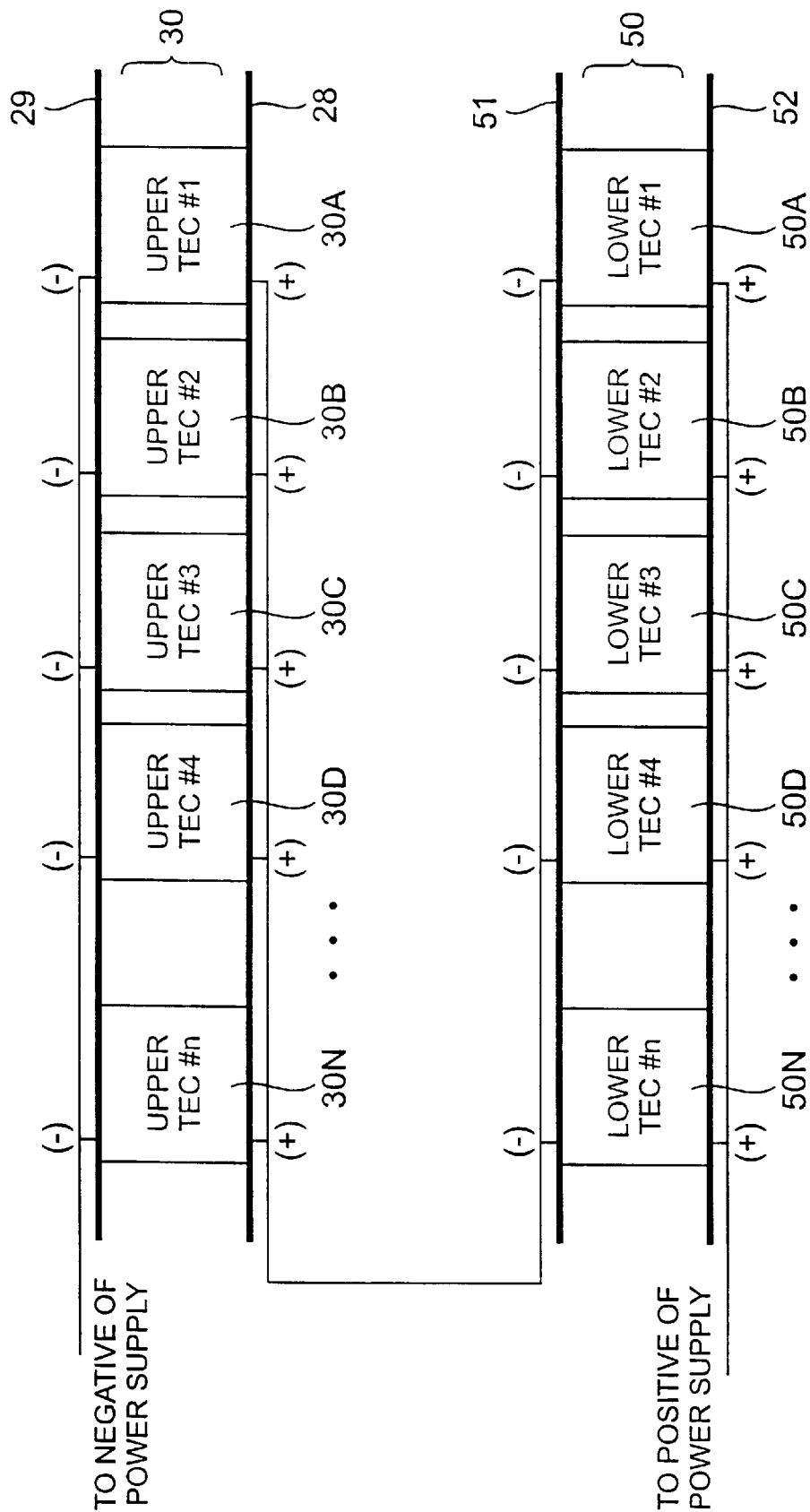
FIG. 2 depicts schematically an upper thermoelectric unit and a lower thermoelectric unit employed in the heat flow meter instrument.

Also referring to FIG. 2, DC power supply 60 provides electric power to upper thermoelectric unit 30 and lower thermoelectric unit 50 connected in series. Both thermoelectric units 30 and 50 include several identical thermoelectric devices each consisting of pairs of an N-type semiconductor and a P-type semiconductor located between two ceramic substrates (a cold face and a hot face). Identical thermoelectric devices 30A, 30B, 30C, 30D, ..., are wired in parallel and thermally coupled to a hot face 28 and a cold face 29. Similarly, identical thermoelectric devices 50A, 50B, 50C, 50D, ..., are electrically connected in parallel and thermally coupled to a cold face 51 and a hot face 52. The DC power supply (e.g., a Vicor power supply, model VI-LF; Sorenson or Lambda power supplies) has an adjustable output to regulate the temperature of the devices. Since power supply 60 provides a DC current to the two thermoelectric units connected in series, approximately the same amount of heat is delivered to specimen 2 by hot face 28 as is taken out of the other side of specimen 2 by cold face 51. The precise amounts of heat added and removed, including the losses, depend also on the operating temperatures of the thermoelectric units.

Figure 3A:
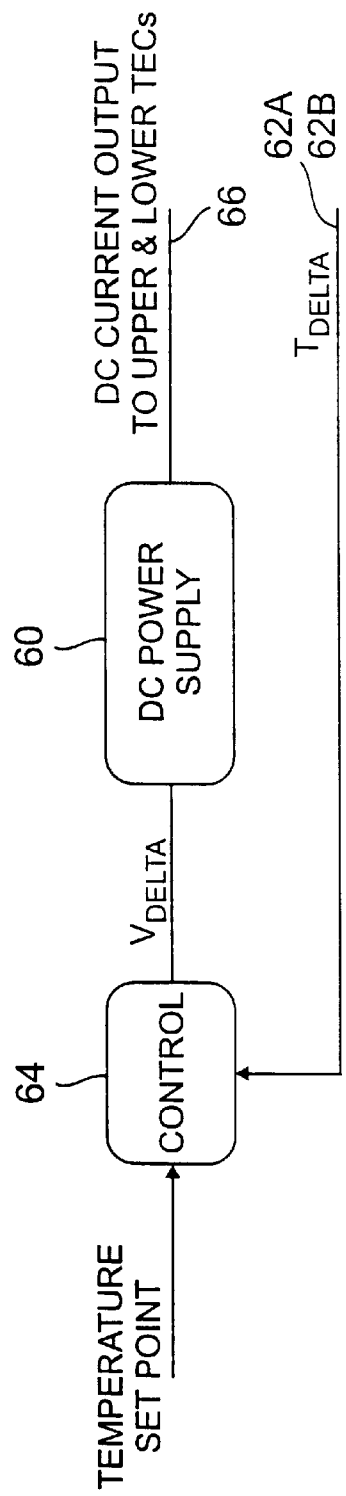
FIGS. 3A and 3B depict schematically a closed loop and an open loop arrangement for controlling power supplied to the thermoelectric units.
Figure 3B:
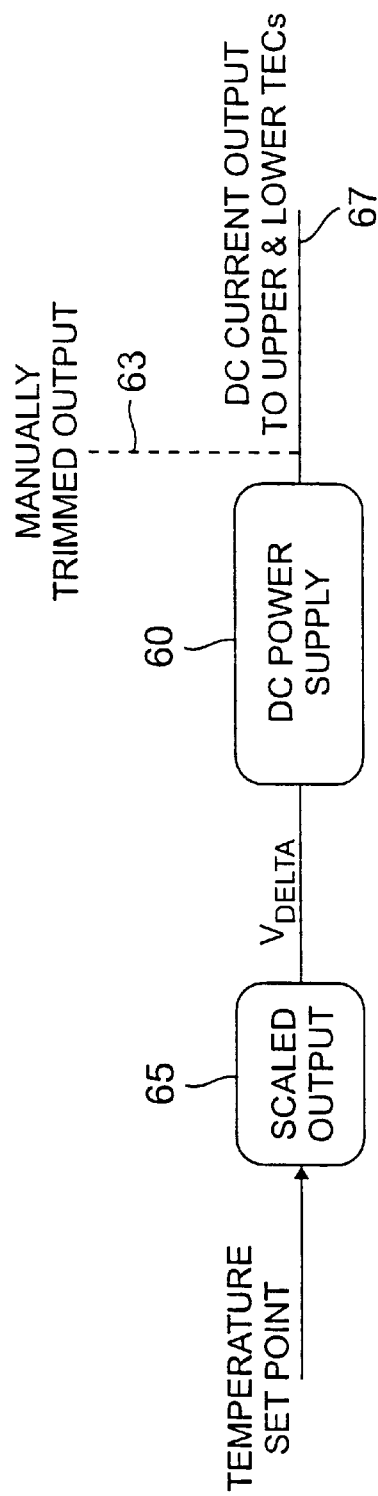

The HFM instrument is constructed to control the temperature across surface plate 16 and 44 in a closed loop, as shown in FIG. 3A, or in an open loop arrangement, as shown in FIG. 3B. The instrument includes at least four K-type (chromel-alumel) thermocouples 18, 20, 46 and 48, which provide the surface plate temperatures for monitoring and controlling purposes. Thermocouples 20 and 48 are connected together in a differential mode, wherein the alumel leads are joined together and the differential temperature ($T_{Delta}$) is measured across the chromel leads. The chromel leads (62A, 62B) are connected to a controller 64. Controller 64 receives a temperature set point either manually or via a computer interface and provides a voltage output signal ($V_{Delta}$) to power supply 60. Power supply 60 provides the corresponding DC current (66) to thermoelectric units 30 and 50. In the open loop arrangement, a scaled output controller 65 provides the control voltage signal ($V_{Delta}$) solely based on the temperature set point. Power supply 60 provides a DC current (67) that may be trimmed (63) to regulate the temperature difference across thermoelectric units 30 and 50. Alternatively, thermocouples 18 and 46 may be replaced by a set of thermocouples distributed over the area of the plates to measure a temperature profile of the surface plates.

The closed thermal loop, which connects upper heat sink 32 and lower heat sink 54 via conduits 34 and 38, enables stable and efficient thermal operation of the HFM instrument. A circulating pump 40 circulates a ethylene glycol/water mixture (or another fluid such as oil or water) between heat sink 54, which is in thermal contact with hot face 52, and heat sink 32, thermally connected to cold face 29. Pump 40 may be a dual head pump MARCH Model 802 (made by March Manufacturing Inc., Glenview, Ill.) One or more thermocouples (37) are used to measure the temperature of the circulating fluid. Heat exchange system 36 is constructed to control the temperature of the fluid ($T_{Mean}$) The temperature control is achieved by either a closed loop arrangement or an open loop control arrangement. At stable conditions, the circulating fluid is maintained at a constant temperature $T_{Mean}$ so that the surface plate temperatures will be controlled at approximately ($T_{Mean}+\frac{1}{2}T_{Delta}$) and ($T_{Mean}-\frac{1}{2}T_{Delta}$). Basically, power supply 60 achieves the desired temperature differential ($T_{Delta}$) across the specimen, and heat exchange system 36 establishes the mean temperature ($T_{Mean}$).

Figure 3C:
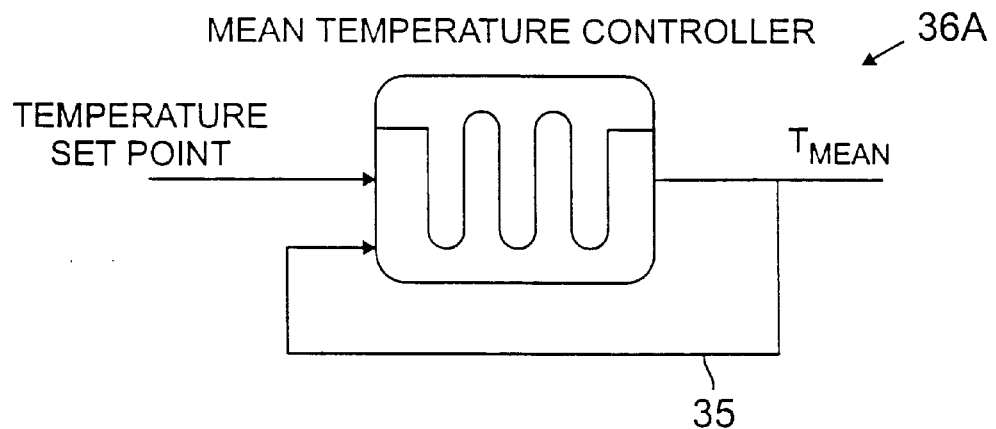
FIGS. 3C and 3D depict schematically heat exchange systems for controlling the mean temperature of the instrument.
Figure 3D:
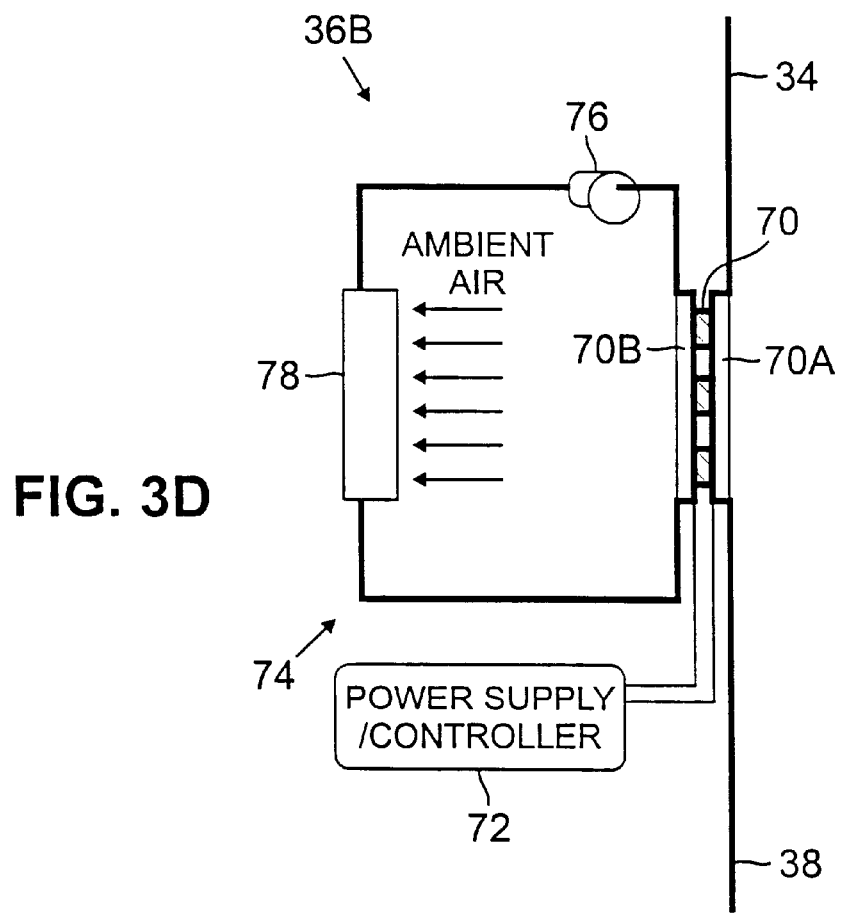

Referring to FIG. 3C, depending on the temperature range of the instrument, a heat exchange system 36A may include a simple electrical heater connected to a controller in a closed loop arrangement 35. Referring to FIG. 3D, alternatively, the temperature of the fluid ($T_{Mean}$) is regulated by a heat exchange system 36B. Heat exchange system 36B includes a thermoelectric heat exchanger 70 with a first face 70A thermally connected to conduits 34 and 38 and a second face 70B thermally connected to an internal thermal loop 74. Thermal loop 74 includes a pump 76 and a radiator 78 cooled, for example, by ambient air. A simplified heat exchange system 36B may have the second face coupled directly to a finned heat sink that provides the heat exchange. A fan may be used to blow air to the finned heat sink. Such a simplified design eliminates the need for internal thermal loop 74, radiator 78 and pump 76.

When the fluid circulating in conduits 34 and 38 is being cooled, a DC power supply 72 provides current to maintain face 70A as a cold face and face 70B as a hot face. Then the heat from hot face 70B is dissipated by thermal loop 74. Alternatively, by reversing the current DC power supply 72 can maintain face 70A as a hot face and face 70B as a cold face. Then the hot face will supply a controlled amount of heat to the fluid circulating in conduits 34 and 38.

The HFM instrument has a test area constructed to accommodate a 12"×12" specimen up to 4" in thickness prepared by standard techniques. (The instrument may have a test area that accommodates a 24"×24" specimen up to 8" in thickness.) The specimen is placed on the top of lower plate assembly 6 in thermal contact with lower heat flux transducer 42. When upper plate assembly 7 is lowered to the specimen surface, the described mechanism allows upper heat flux transducer 14 to conform with the specimen surface. The thickness of the specimen is measured by a linear potentiometer LX-PA-4.7 (made by Unimeasure, Inc., Corvallis, Oreg.). The linear potentiometer (not shown in FIG. 1) connects the center of plate 8 and the center of the moving upper plate assembly 7 and thus measures the distance between plate 8 and plate assembly 7. This distance corresponds to an average thickness of specimen 2. (Alternatively, a linear potentiometer may be connected to each corner of plate assembly 7. The average thickness is then calculated from the data measured by the four potentiometers.)

Figure 4:
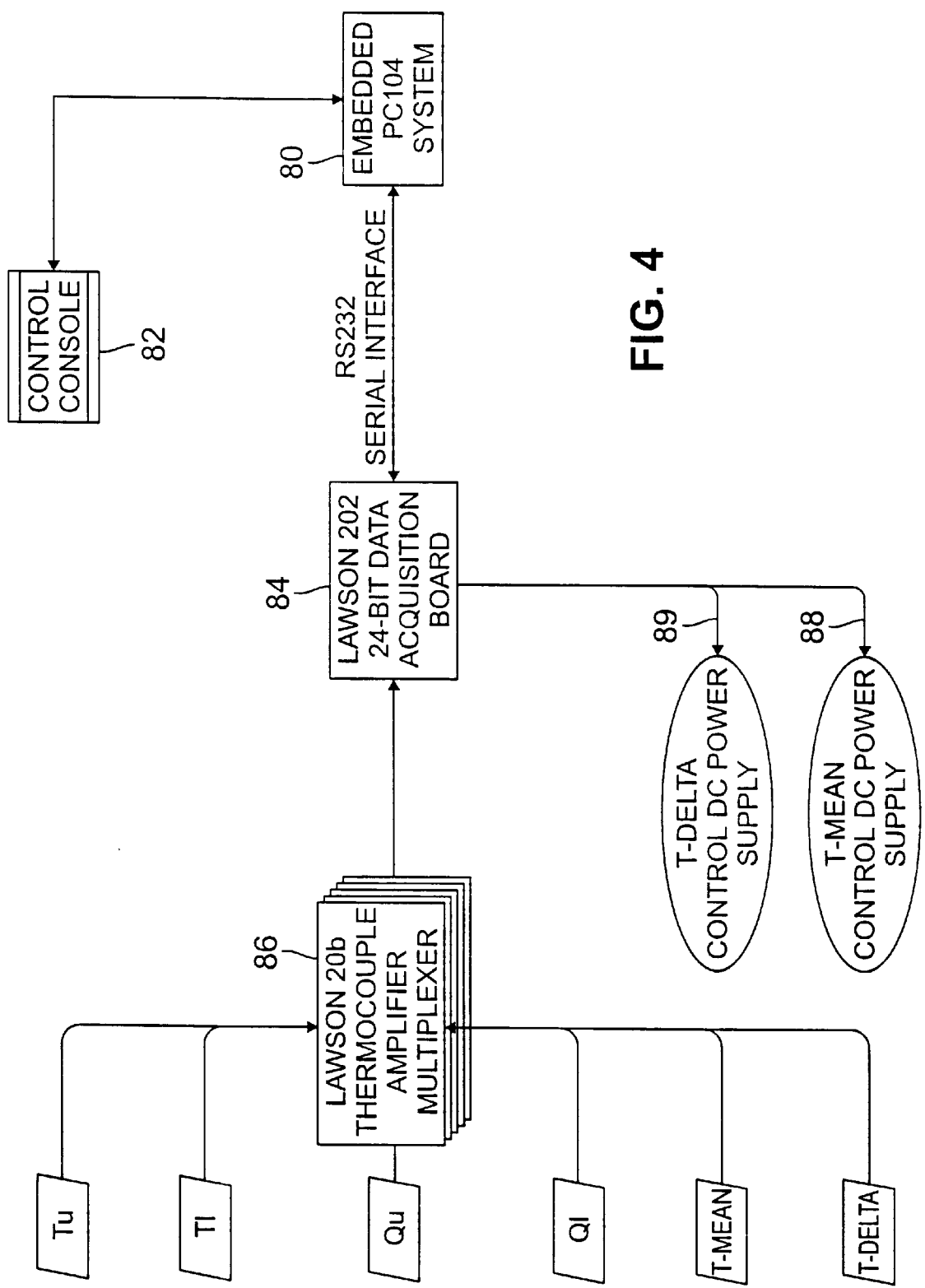
FIG. 4 depicts schematically data acquisition hardware of the heat flow meter instrument.

Referring to FIG. 4, the operation of the HFM instrument is controlled by an embedded PC-104 system 80 connected to a control console 82. (A standalone 486 or 586 personal computer may be used instead.) Computer 70 is connected to a data acquisition board 84 via an RS 232 serial interface. Board 84 is a Lawson model 202 (24 bit Data Acquisition Board), which is connected to a amplifier/multiplexer system 86 (Lawson, model 20b, made by Lawson Labs., Inc., Kalispell, Mont.). The system receives sensor values $T_u$ and $T_l$ measured by thermocouples 18 and 46, respectively, $T_{Delta}$ measured across the chromel leads of thermocouples 20 and 48, and $T_{Mean}$ measured by thermocouple 37. The system also acquires values $Q_u$ and $Q_l$ from heat flux transducers 14 and 42, respectively, and the thickness value from the linear potentiometer.

Computer 80 runs an automation software, which enables automatic data acquisition and temperature control. Based on a control algorithm, computer 80 sends control signals to the Lawson 202 board (control 64 of FIG. 3A for differential temperature control), which, in turn, sends analog (0–5 Volt) control signals 88 and 89 to DC power supply 60 and heat exchange system 36, respectively.

Figure 5:
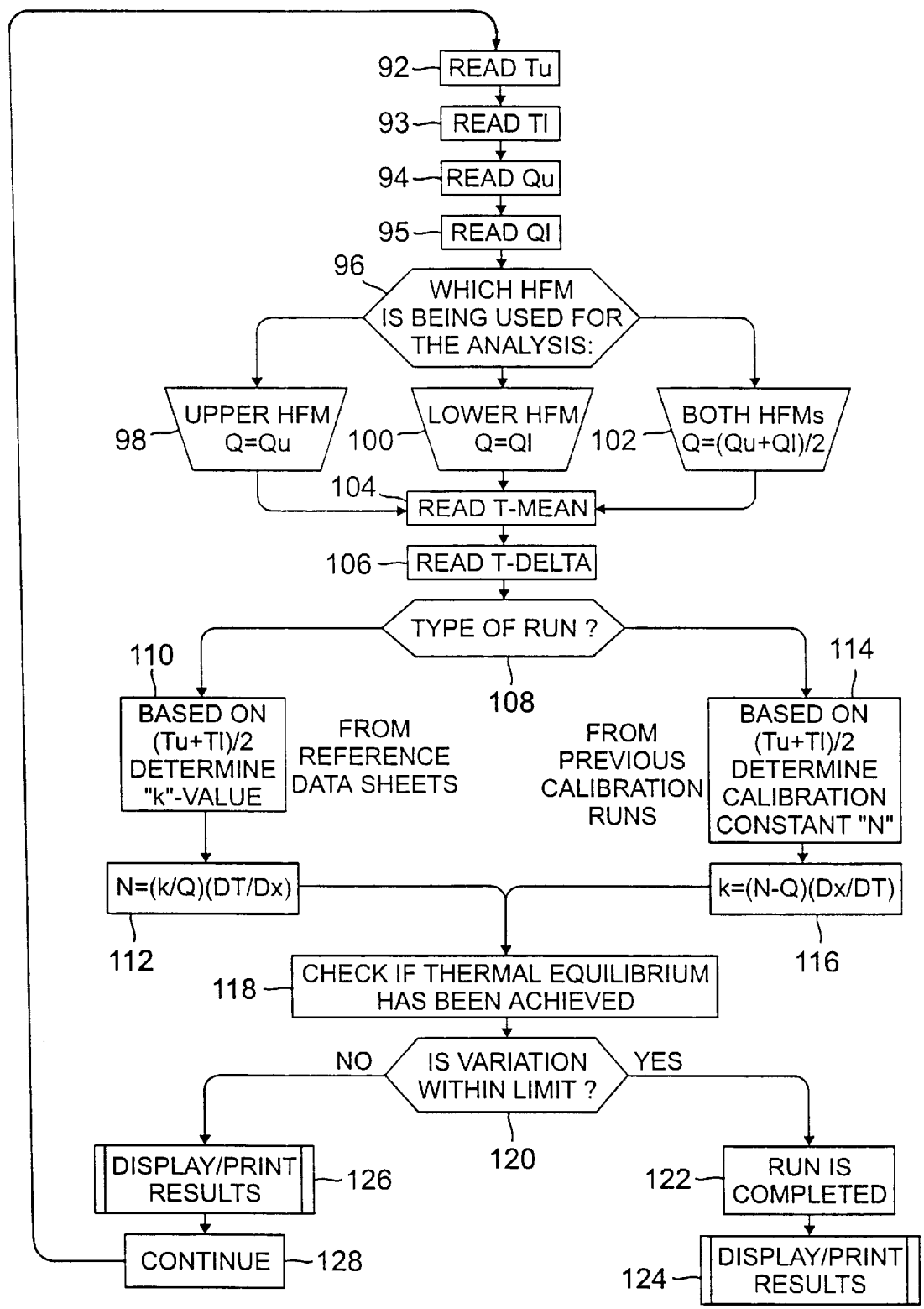
FIG. 5 is a flowchart of data acquisition and reduction.

Referring to FIG. 5, the software performs the data acquisition and evaluation as follows. In steps 92 through 95, the processor reads values $T_u$, $T_l$, $Q_u$, and $Q_l$. Depending on the heat flux transducer employed (step 96), the computer assigns the specimen heat, $Q=Q_u$ (step 98 if only the upper heat flux transducer is used), $Q=Q_l$ (step 100 if only the lower heat flux transducer is used), or $Q=\frac{1}{2}(Q_l+Q_u)$ (step 102 if both the upper and lower heat flux transducers are used). The computer reads values $T_{Mean}$ and $T_{Delta}$ in steps 104 and 106. Values of $T_{Mean}$ and $T_{Delta}$ are used as dedicated feedback sensors in the control algorithm. These values are compared to $\frac{1}{2}(T_l+T_u)$ and $(T_u-T_l)$, respectively, when adjusting the set points of $T_{Mean}$ and $T_{Delta}$.

In a calibration procedure, a reference sample with known thermal conductivity is measured to calibrate the instrument. The computer first recalls the thermal conductivity value (k) corresponding to the reference sample at the $\frac{1}{2}(T_l+T_u)$ temperature (step 110). Next, the computer calculates the heat flux transducer calibration factor, N, based on Eq. 2 (step 112).

$$N = \frac{k}{Q} \cdot \frac{\Delta T}{\Delta X} \tag{2}$$

In a measurement procedure that characterizes a specimen, the computer first recalls the calibration factor (N) corresponding to the calibration temperature $\frac{1}{2}(T_l+T_u)$ of the instrument (step 114). Next, the computer calculates the thermal conductivity value, k (step 116), as follows:

$$k = N \cdot Q \frac{\Delta X}{\Delta T} \tag{3}$$

All data can be displayed on the screen and printed on a printer (steps 124 or 126).

Figure 6:
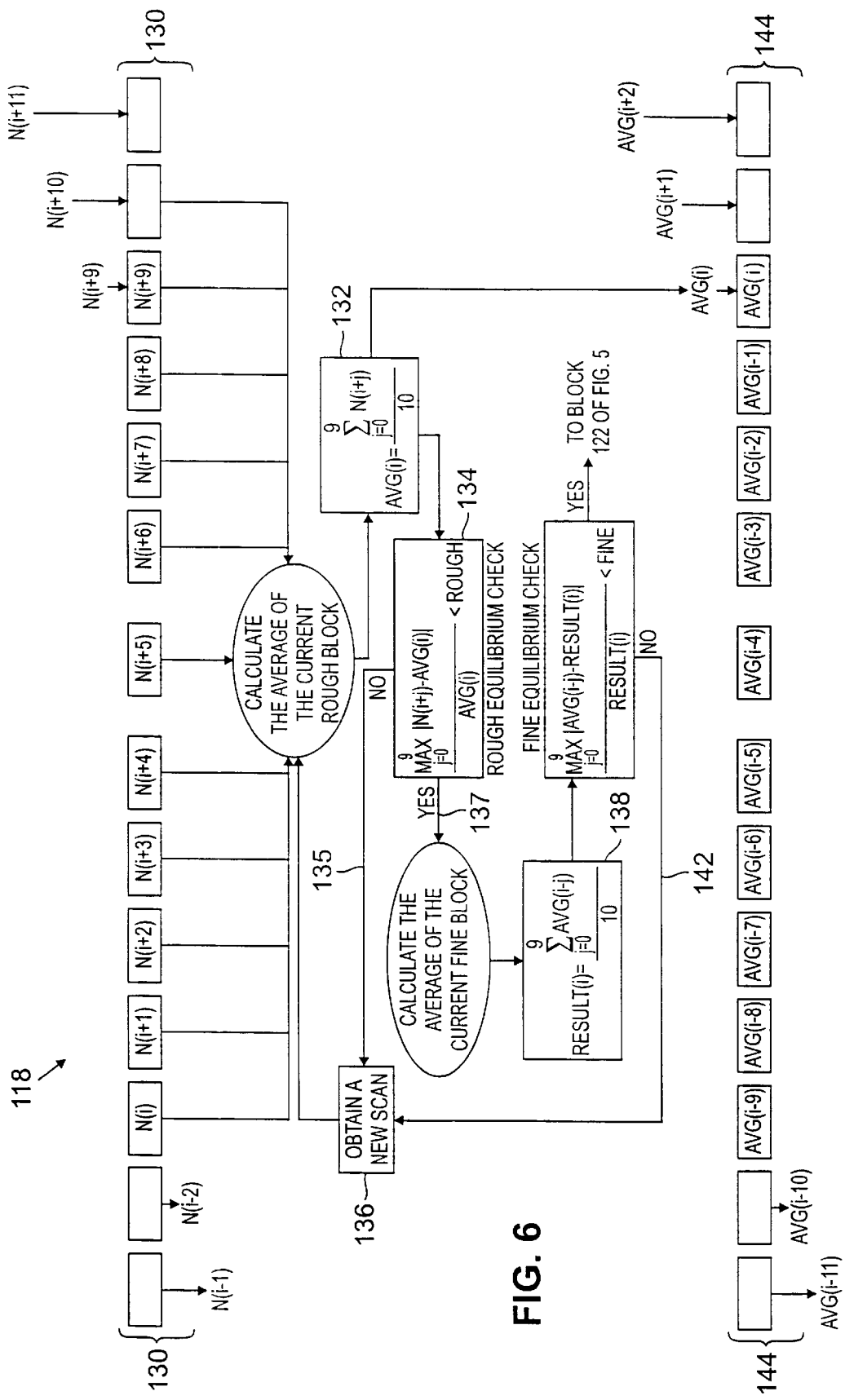
FIG. 6 is a flowchart of an algorithm for determining thermal equilibrium of the instrument.

Also referring to FIG. 6, when the instrument operates in a steady state mode, the computer checks the thermal equilibrium by employing an algorithm 118. The operator can control the level of thermal equilibrium by initially selecting "rough" and "fine" deviation values for N or k. For example, during the calibration procedure, the computer recalls ten most recent values of N (field 130), calculates their average, Avg(i) (step 132) and stores Avg(i) in field 144. Then, the computer tests "rough equilibrium" (step 134). If any of the measured value ($N_i$) of the ten most recent values stored in field 130 is outside the selected "rough" deviation value (135), the instrument performs a new scan (136) and stores the calculated value N (Equation 2) in field 130. If the ten most recent values ($N_{i+j}$) are within the selected "rough" deviation value (137), the computer calculates the average of the current "fine" block, i.e., Result(i) in step 138. In step 140, the computer evaluates whether all of the last ten values stored in field 144 are within the selected "fine" deviation value. If each value is within the "fine" deviation value, the system has reached thermal equilibrium, and the last calculated value, Result(i), is the final value. Otherwise, the instrument performs a new scan (142). The same equilibrium algorithm is performed during the measurement run for k values.

Figure 7A:
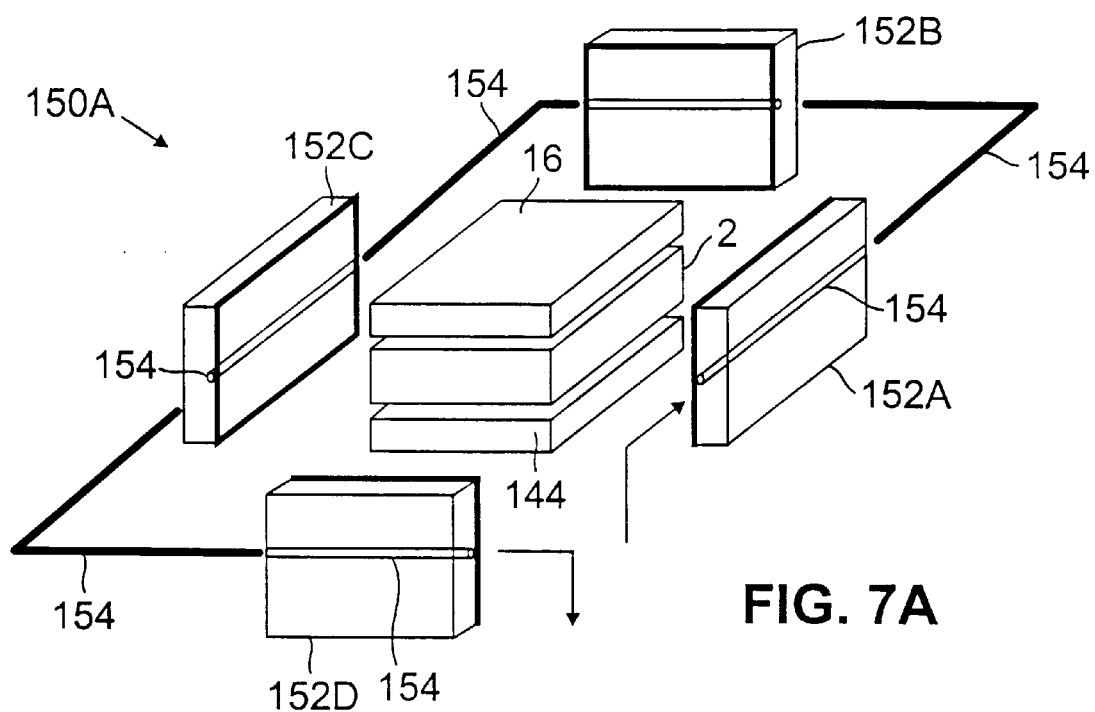
FIGS. 7A and 7B depict schematically embodiments of the test section of a guarded heat flow meter instrument.
Figure 7B:
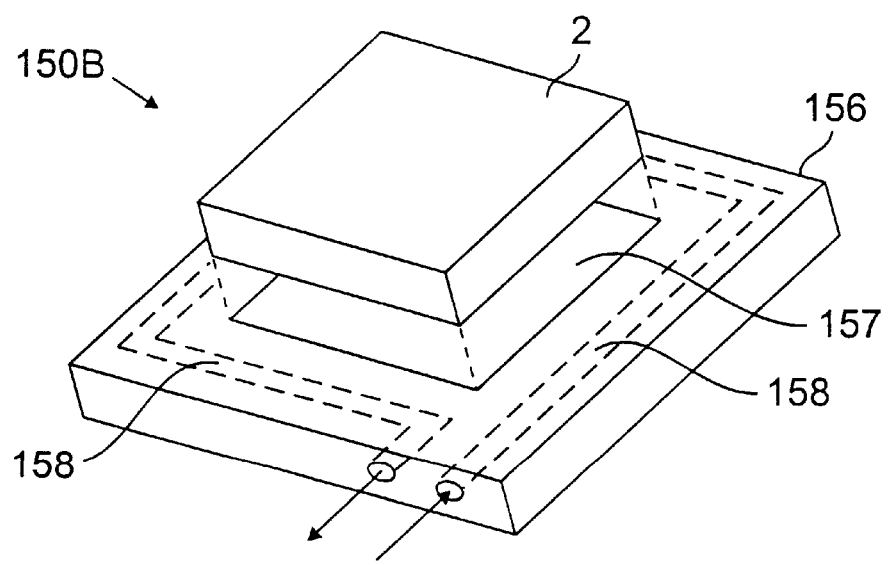

Referring to FIGS. 7A and 7B, in another embodiment, the HFM instrument is a guarded heat flow meter. The test section (150A or 150B) of the instrument is constructed to limit lateral heat loss from specimen 2. Test section 150A includes four heat guards 154A, 154B, 154C, and 154D thermally connected to conduits 154. Conduits 154 circulate the fluid maintained at $T_{Mean}$. During the measurement, the heat guards surround specimen 2, sandwiched between upper surface plate 16 and lower surface plate 44, and thus limit the lateral heat loss from the specimen. Alternatively, test section 150B includes a single heat guard 158 with an opening 157 made to fit specimen 2. Heat guard 158 again includes a set of conduits 158 for the circulating fluid. (This instrument can operate according to the F 433 standard testing method, published in the Annual Book of ASTM Standards.) The test section is constructed for a quick exchange of the specimen to be measured either by the above-described, steady state method or a transient temperature method.

In another embodiment, the instrument operates in a transient temperature mode. This transient temperature mode may be used with HFM instrument 1 described above or with any standard heat flow meter instrument. The transient temperature mode is employed in a quick measurement of the thermal conductivity without waiting until the system reaches the steady state. For example, when performing quality control on a production line of thermal insulation materials, the on line testing related to process control requires a relatively short measurement time. Thus the computer does not execute algorithm 118 (of FIG. 6), but executes a predictive algorithm 170 (of FIG. 9). During the predictive algorithm, the instrument measures a transient data response over a relatively short time period and calculates the expected steady-state value of thermal conductivity (k), which is a characteristic of the tested material.

Figure 8A:
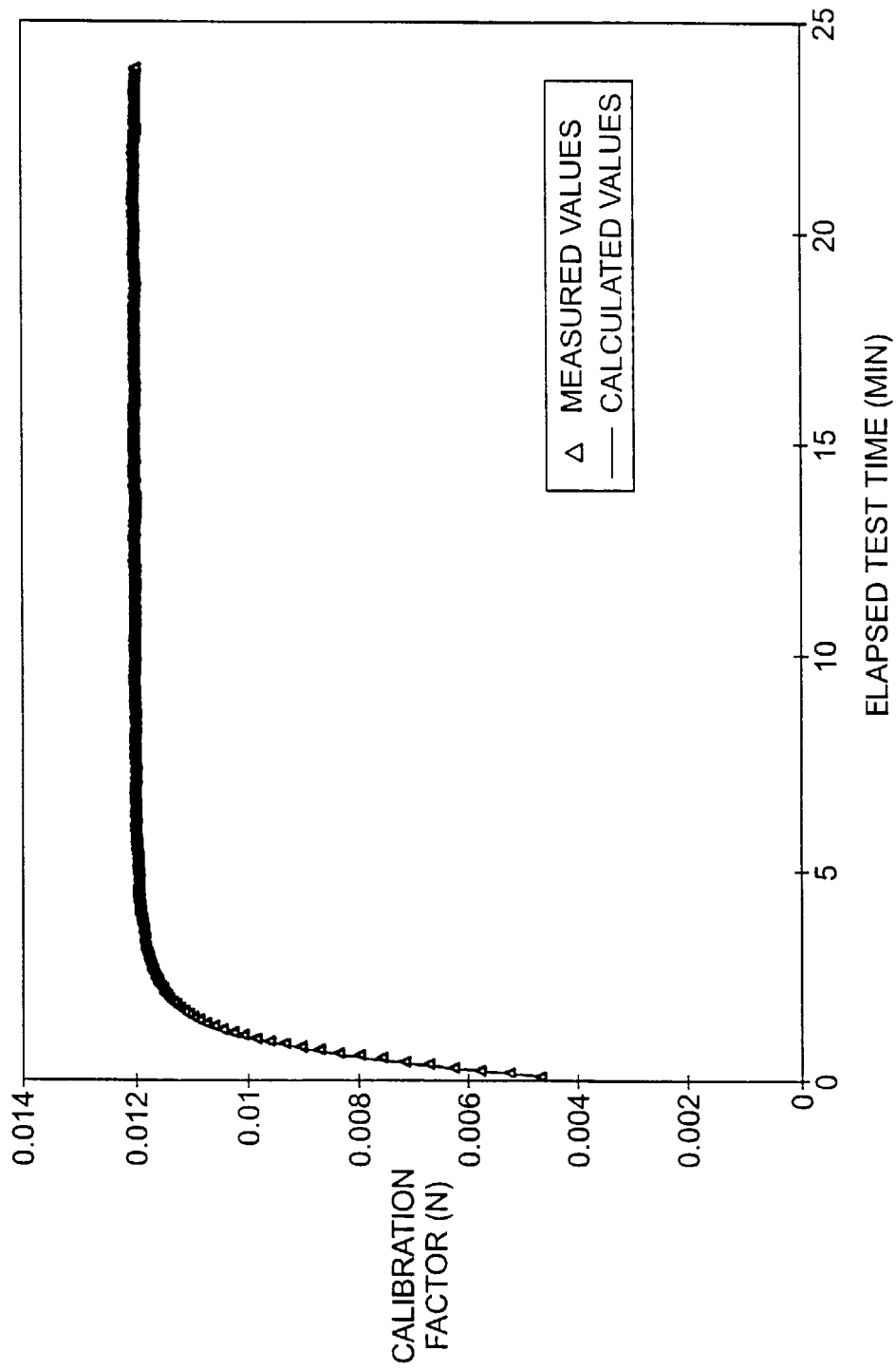
FIGS. 8A and 8B depict a measured functional dependence of the calibration factor and its deviation from the steady state value under transient temperature conditions, respectively.
Figure 8B:
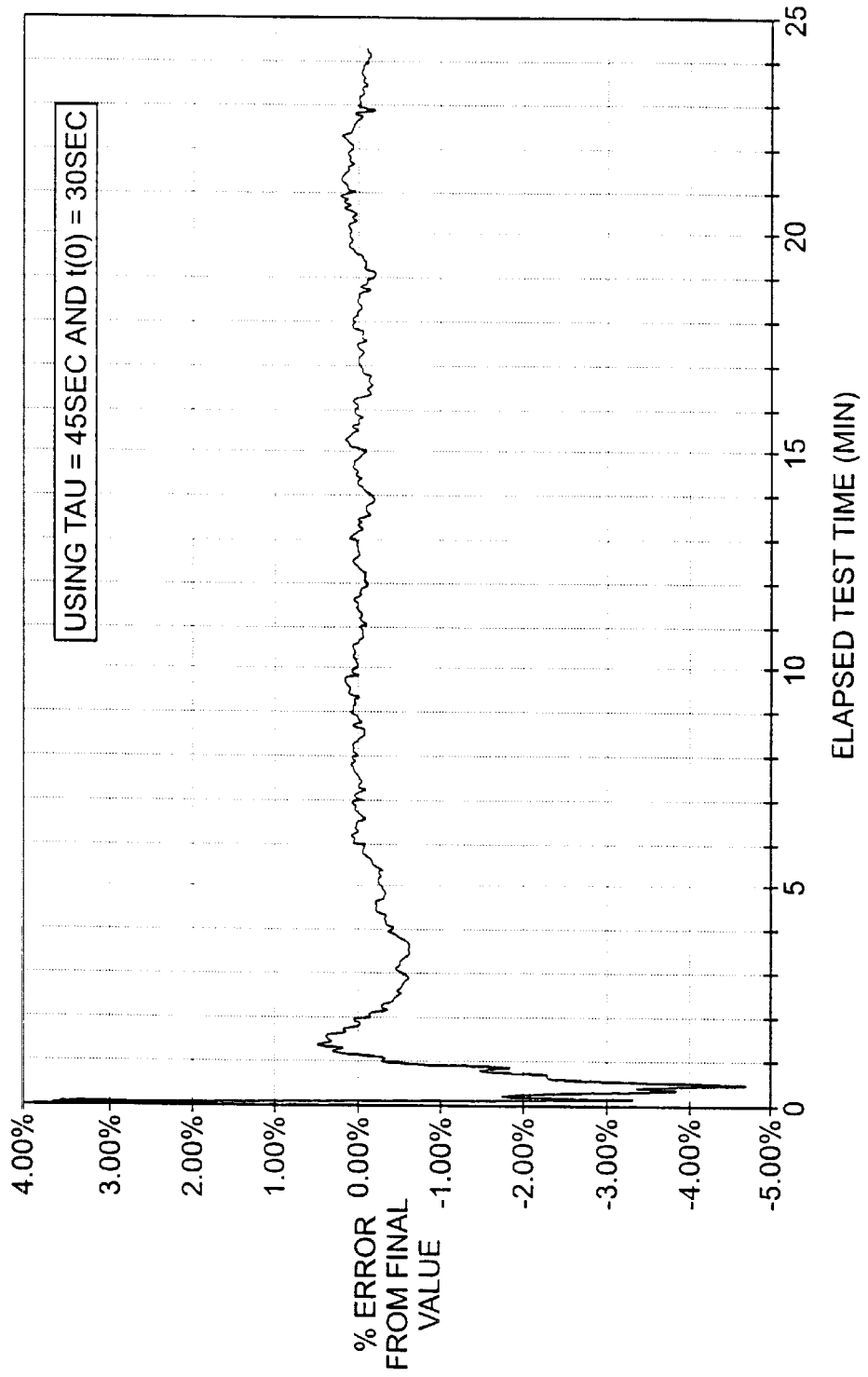

When a new specimen is loaded into the test section with plates 16 and 44 at the selected temperatures, the specimen undergoes a step function change in its surface temperatures. The thermal behavior of the specimen can be approximated by an electric RC circuit connected to a DC voltage, wherein $R_{th}$ is a modeled thermal resistance and $C_{th}$ is a modeled thermal capacitance of the specimen. Using the well known relationship of a charging capacitance in a serial RC circuit, the thermal conductivity k can be approximated as follows:

$$k_{\text{final}} = \frac{k(t)}{1 - \exp(-t/\tau)} \qquad (4)$$

wherein k(t) is an instantaneous value at time t after loading the specimen, $k_{final}$ is the steady state value, and $\tau$ is the product $R_{th} \times C_{th}$. The same relationship can be used for the calibration factor (N) during the calibration procedure as is confirmed in FIG. 8A. FIG. 8A shows instantaneous values of the calibration factor N(t) measured on a 12"×12"×1" Styrofoam® sample (triangles) and the predicted RC functional dependance (N(t) calculated from the Equation 4 type relationship). FIG. 8B shows a time dependence (162) of the percent error of the predicted final value relative to the steady-state value of k. After about one minute, the predicted value is within 1% of the steady-state value.

Figure 9:
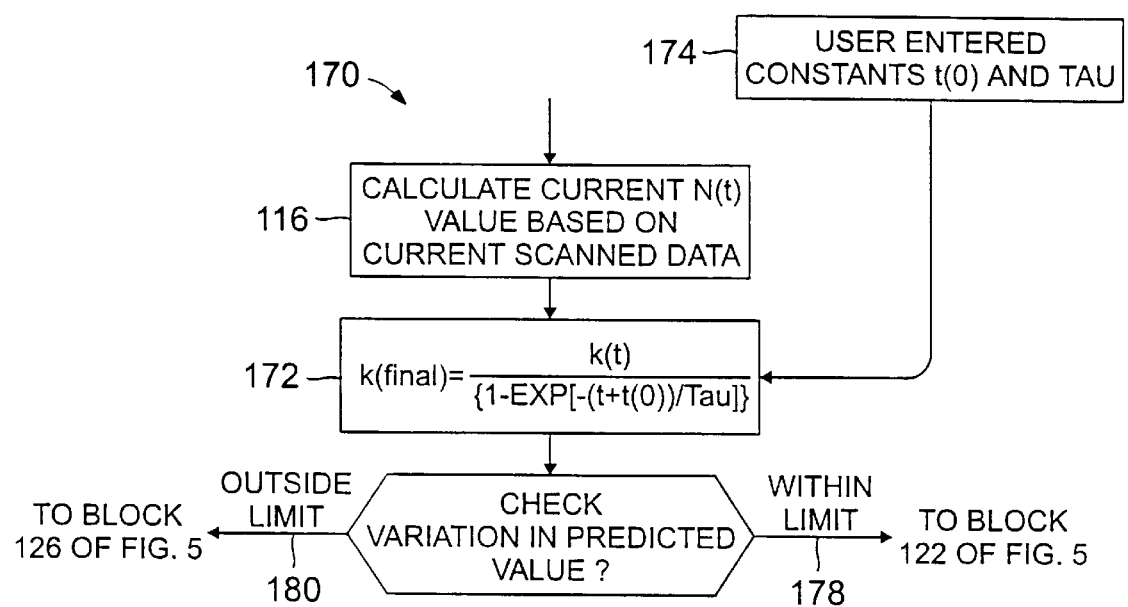
FIG. 9 is a flowchart of a predictive algorithm employed in a transient temperature mode.

Referring to FIG. 9, in the transient temperature mode, the computer executes predictive algorithm 170 instead of the equilibrium algorithm (shown as step 118 in FIG. 5). The computer calculates an instantaneous thermal conductivity k(t) (step 116). In step 174, the computer recalls the value of $\tau$ from the memory. Then, the computer calculates the predicted value $k_{final}$ using Equation 5 (step 172).

$$k_{final} = k(t)[1 - \exp\left[-(t+t(0))/\tau\right]] \qquad (5)$$

wherein $\tau = R_{th} \times C_{th}$, t(0) is the time the specimen was exposed to the temperatures of lower plate assembly 6 and upper plate assembly 7 prior to starting the test, and t is the elapsed test time at which data was collected. Values $R_{th}$ and $C_{th}$ are determined for each material by measuring the time dependance of k until the steady state of the specimen is achieved (see FIG. 8A). Both $R_{th}$ and $C_{th}$ depend on the type of material and on the specimen size.

In step 176, the computer may check for variations in the predicted value. If two subsequent values $k_{final}$ are within a selected limit (178), the transient temperature run is completed. If the values $k_{final}$ are outside of a selected limit (180), the instrument reads new values $T_u$, $T_l$, $Q_u$, and $Q_l$ and repeats the calculation cycle. Therefore, the transient temperature mode permits rapid evaluation of tested samples.

Other embodiments of the HFM instrument may include different combinations of the features suggested above and features described in prior art. Additional embodiments are within the following claims.

What is claimed is:

1. An apparatus for measuring a thermal property of a specimen comprising:

a first thermoelectric device and a second thermoelectric device, each said device being thermally coupled to a hot plate and a cold plate;

a heat flow transducer, thermally connectable to a specimen, the combination of said heat flow transducer and said specimen being positionable in thermal contact between said hot plate of said first thermoelectric device and said cold plate of said second thermoelectric device, said heat flow transducer being constructed and arranged to measure heat flowing through said specimen from said hot plate to said cold plate;

an electric power supply connected to provide simultaneously electric power to said first and second thermoelectric devices to maintain said plates at selected temperatures; and a processor connected to receive from said heat flow transducer a signal corresponding to said measured heat; said processor being further programmed to calculate a thermal property of said specimen based on said temperatures and said measured heat.

2. The apparatus of claim 1 wherein said thermoelectric device includes pairs of N-type and P-type semiconductors.

3. The apparatus of claim 1 further comprising a first temperature sensor and a second temperature sensor located in thermal contact with said hot plate of said first thermoelectric device and a cold plate of said second thermoelectric device, respectively.

4. The apparatus of claim 1 further comprising:

a heat exchange system, thermally connected to said cold plate of said first thermoelectric device or said hot plate of said second thermoelectric device and constructed and arranged to transfer heat to or from said plates.

5. An apparatus for measuring thermal properties of a specimen comprising:

a first thermoelectric device and a second thermoelectric device, each said device being thermally coupled to a hot plate and a cold plate;

a heat flow transducer, thermally connectable to a specimen, the combination of said heat flow transducer and said specimen being positionable in thermal contact between said hot plate of said first thermoelectric device and said cold plate of said second thermoelectric device, said heat flow transducer being constructed and arranged to measure heat flowing through said specimen from said .hot plate to said cold plate;

at least one electric power supply connected to provide controlled amounts of electric power to said first thermoelectric device and said second thermoelectric device to maintain said plates at selected temperatures;

a closed loop heat exchange system, thermally connecting said cold plate of said first thermoelectric device and said hot plate of said second thermoelectric device, constructed and arranged to transfer heat between said plates; and a processor connected to receive from said heat flow transducer a signal corresponding to said measured heat, said processor being further programmed to calculate a thermal property of said specimen based on said temperatures and said measured heat.

6. The apparatus of claim 5 wherein said closed loop heat exchange system includes a first set of conduits thermally connected to said cold plate of said first thermoelectric device and a second set of conduits thermally connected to said hot plate of said second thermoelectric device, said conduits constructed to convey a heat exchange fluid in a closed loop arrangement; and a fluid pump being constructed to circulate said fluid.

7. The apparatus of claim 6 wherein said closed loop heat exchange system includes a heater constructed to heat said heat exchange fluid to a selected temperature.

8. The apparatus of claim 6 wherein said closed loop heat exchange system includes a refrigerator constructed to cool said heat exchange fluid to a selected temperature.

9. The apparatus of claim 1, 3, 4 or 5 further comprising:

a second heat flow transducer constructed to measure a flow of heat, said first and said second heat flow transducer arranged in thermal contact with both sides of said specimen.

10. The apparatus of claim 1, 4 or 6 further comprising a thermal guard member constructed and arranged to prevent a lateral heat loss from said specimen.

11. The apparatus of claim 10 wherein said thermal guard member includes a set of conduits connected to said closed loop heat exchange system and constructed to convey said heat exchange fluid.

12. The apparatus of claim 1 wherein said electric power supply is a current supply constructed to deliver DC current to said first thermoelectric device and said second thermoelectric device connected in series.

13. The apparatus of claim 1 wherein said electric power supply is a voltage source connected to deliver DC voltage to said first thermoelectric device and said second thermoelectric device.

14. The apparatus of claim 1 or 5 further comprising a potentiometer constructed and arranged to provide a signal corresponding to the thickness of said specimen.

15. The apparatus of claim 1 or 5 wherein said processor is further arranged to calculate said thermal property under steady-state thermal conditions.

16. The apparatus of claim 1 or 5 wherein said processor is further arranged to calculate a predicted steady-state value of said thermal property under transient thermal conditions.

17. The apparatus of claim 16 wherein said processor is further arranged to employ a selected equation predicting thermal behavior of said specimen under said transient thermal conditions.

18. An apparatus for measuring a thermal property of a specimen comprising:

a first heat generating device thermally coupled to a hot plate and a second heat generating device thermally coupled to a cold plate;

a first temperature sensor and a second temperature sensor located in thermal contact with said hot plate and said cold plate, respectively;

a heat flow transducer, thermally connectable to a specimen, constructed and arranged to measure heat flowing through said specimen before reaching steady-state thermal conditions, the combination of said heat flow transducer and said specimen being positionable in thermal contact between said hot plate and said cold plate;

at least one electric power supply connected to provide controlled amounts of electric power to said first device and said second device to maintain said plates at selected temperatures; and a processor connected to receive from said heat flow transducer a signal corresponding to said measured heat, said processor being further programmed to calculate a predicted steady-state value of a thermal property of said specimen under transient thermal conditions based on said measured heat and said temperatures.

19. The apparatus of claim 18 further comprising at least one heat exchange system, thermally connected to said cold plate and said hot plate, constructed and arranged to maintain said plates at said selected temperatures.

20. A method of measuring a thermal property of a specimen comprising:

providing a first thermoelectric device and a second thermoelectric device, each said device being thermally coupled to a hot plate and a cold plate, said thermoelectric devices being connected to an electric power supply;

positioning a specimen, thermally coupled to a heat flow transducer, in thermal contact between said hot plate of said first thermoelectric device and said cold plate of second thermoelectric device;

establishing selected temperatures of said hot plates and said cold plates by providing simultaneously electric power from said power supply to said first thermoelectric device and said second thermoelectric device;

measuring heat flowing through said specimen from said hot plate of said first thermoelectric device to said cold plate of said second thermoelectric device by utilizing said heat flow transducer; and calculating a thermal property of said specimen based on said measured heat and said temperatures.

21. The method of claim 20 further comprising:

providing a closed loop heat exchange system thermally connected to said cold plate of said first thermoelectric device and said hot plate of said second thermoelectric device; and transferring heat between said cold plate of said first thermoelectric device and said hot plate of said second thermoelectric device.

22. The method of claim 21 wherein said heat transferring step includes circulating a heat exchange fluid in a closed loop arrangement.

23. The method of claim 22 further including preventing lateral heat loss from said specimen.

24. The method of claim 23 wherein said preventing step includes circulating said heat exchange fluid in a thermal guard member disposed around said specimen.

25. The method of claim 22 further including heating said circulating fluid to a selected temperature.

26. The method of claim 22 further including cooling said circulating fluid to a selected temperature.

27. The method of claim 20, 21 or 22 further providing a second heat flow transducer, and the method further comprising positioning said first and said second heat flow transducer in thermal contact with both sides of said specimen, and determining heat flowing through said specimen by utilizing said second heat flow transducer.

28. The method of claim 20 further providing first temperature sensor and a second temperature sensor, and the method further comprising positioning said first and said second temperature sensor in thermal contact with said hot plate of said first thermoelectric device and said cold plate of said second thermoelectric device, respectively, and measuring temperatures of said hot plate and said cold plate.

29. The method of claim 20 wherein said establishing step includes providing a selected amount of current to said first thermoelectric device and said second thermoelectric device.

30. The method of claim 20 wherein said establishing step includes maintaining a selected voltage across said first thermoelectric device and said second thermoelectric device.

31. The method of claim 20 further including measuring the thickness of said specimen.

32. The method of claim 20 further including calculating said thermal property under steady-state thermal conditions.

33. The method of claim 20 further including calculating a predicted steady-state value of said thermal property under transient thermal conditions.

34. The method of claim 33 wherein said calculating step includes employing a selected equation that predicts thermal behavior of said specimen under transient thermal conditions.

35. A method of measuring a thermal property of a specimen comprising:

provide a first heat generating device thermally coupled to a hot plate and a second heat generating device thermally coupled to a cold plate; a first temperature sensor and a second temperature sensor located in thermal contact with said hot plate and said cold plate, respectively, said devices being connected to at least one electric power supply;

positioning a specimen, thermally coupled to a heat flow transducer, in thermal contact between said hot plate and said cold plate;

establishing selected temperatures of said hot and cold plates by providing electric power to said first device and said second device;

measuring heat flowing through said specimen by utilizing said heat flow transducer before reaching steady-state thermal conditions; and calculating a predicted steady-state value of a thermal property of said specimen under transient thermal conditions based on said measured heat and said temperatures.

36. The method of claim 35 further comprising:

providing at least one heat exchange system thermally connected to said cold plate and said hot plate; and transferring heat to or from said plates to maintain said plates at said selected temperatures.

\* \* \* \* \*